(12) United States Patent
Hierold et al.

(10) Patent No.: US 10,974,039 B2
(45) Date of Patent: Apr. 13, 2021

(54) METHOD FOR THE MANUFACTURING OF A CARRYING DEVICE, CARRYING DEVICE, SYSTEM FOR DETECTION OF A PHYSICAL PARAMETER AND METHOD FOR DETECTION OF A PHYSICAL PARAMETER

(71) Applicant: ETH Zürich, Zürich (CH)

(72) Inventors: Christofer Hierold, Baden (CH); Christian Peters, Zürich (CH); Silvan Staufert, Zofingen (CH)

(73) Assignee: ETH ZÜRICH, Zürich (CH)

( * ) Notice: Subject to any disclaimer, the term of this patent is extended or adjusted under 35 U.S.C. 154(b) by 224 days.

(21) Appl. No.: 16/086,620

(22) PCT Filed: Mar. 20, 2017

(86) PCT No.: PCT/EP2017/056557
§ 371 (c)(1),
(2) Date: Sep. 20, 2018

(87) PCT Pub. No.: WO2017/162588
PCT Pub. Date: Sep. 28, 2017

(65) Prior Publication Data
US 2019/0070347 A1    Mar. 7, 2019

(30) Foreign Application Priority Data
Mar. 23, 2016    (EP) ..................... 16161976

(51) Int. Cl.
*G01L 19/14*    (2006.01)
*A61B 5/00*    (2006.01)
(Continued)

(52) U.S. Cl.
CPC ............. *A61M 60/50* (2021.01); *A61B 5/021* (2013.01); *A61B 5/0215* (2013.01);
(Continued)

(58) Field of Classification Search
CPC ........ A61B 2562/12; A61B 2562/0247; A61B 2562/164; A61B 2562/168; A61B 5/6876;
(Continued)

(56) References Cited

U.S. PATENT DOCUMENTS 5,902,248 A    5/1999 Millar et al.
6,367,333 B1    4/2002 Bullister et al.
(Continued)

FOREIGN PATENT DOCUMENTS

WO    WO-0065984 A1 * 11/2000 ........... A61B 5/6876
WO    WO2000065984 A1    11/2000
WO    WO2015126703 A1    8/2015

*Primary Examiner* — Catherine B Kuhlman
(74) *Attorney, Agent, or Firm* — Soroker Agmon Nordman

(57) ABSTRACT

The invention relates to a method for the manufacturing of a carrying device, a carrying device, a system for detection and a method for detection of at least one physical parameter and/or chemical composition. A method for the manufacturing of a carrying device for reception of at least one sensor is presented, in which a receiving body with a surface to be coated is provided. In the receiving body, a space is provided which is open on the side of this surface. A second body with a sealing surface is provided. This sealing surface is positioned in such a manner that the surface to be coated of the receiving body is sealed by the second body at least in the circumference of the space in the receiving body. A formable or moldable filling material is provided in the space in such a manner that the filling material forms a surface shaped complementary to the sealing surface of the second body, closing the space. At least the volume of the filling material contacting the sealing surface of the second body is solidified. The sealing surface of the second body is removed from the surface to be coated as well as from the
(Continued)

Figure 1:
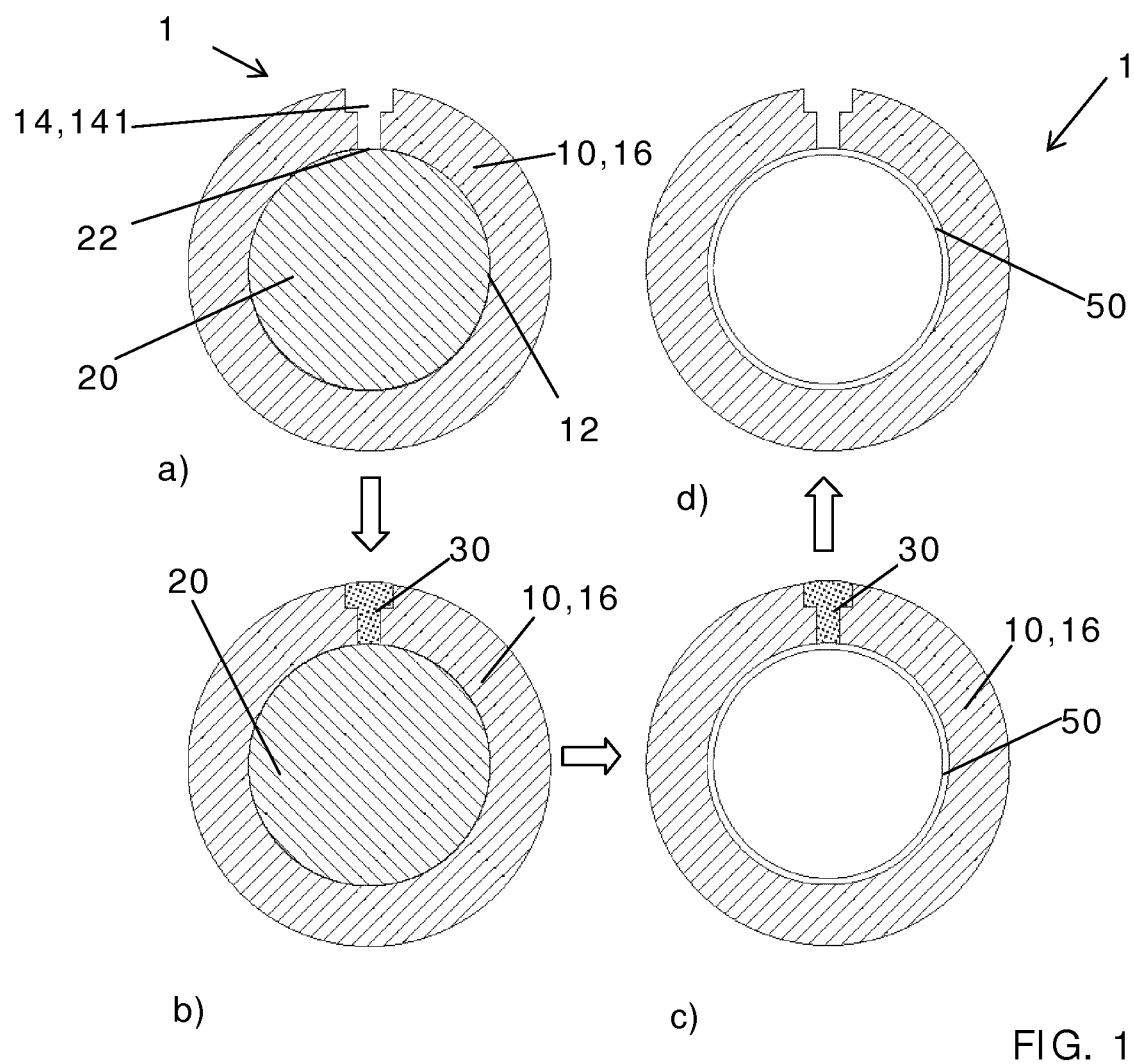

surface provided by the filling material. The surface to be coated is coated such that a membrane is provided, sealing the space.

7 Claims, 2 Drawing Sheets

(51) Int. Cl.
    *A61M 60/50*     (2021.01)
    *A61B 5/0215*     (2006.01)
    *A61M 60/148*     (2021.01)
    *A61M 60/205*     (2021.01)
    *A61B 5/021*     (2006.01)
    *A61B 5/024*     (2006.01)
    *A61B 5/145*     (2006.01)
    *A61B 5/1473*     (2006.01)

(52) U.S. Cl.
    CPC ......... *A61B 5/6876* (2013.01); *A61M 60/148* (2021.01); *A61M 60/205* (2021.01); *G01L 19/141* (2013.01); *A61B 5/02438* (2013.01); *A61B 5/1473* (2013.01); *A61B 5/14542* (2013.01); *A61B 2562/028* (2013.01); *A61B 2562/0247* (2013.01); *A61B 2562/12* (2013.01); *A61B 2562/168* (2013.01); *A61B 2562/18* (2013.01); *A61M 2205/3334* (2013.01); *A61M 2205/3344* (2013.01); *A61M 2207/00* (2013.01); *A61M 2230/06* (2013.01); *A61M 2230/205* (2013.01)

(58) Field of Classification Search
    CPC ...... A61B 5/021; A61B 5/0215; A61M 1/122; A61M 1/1012; A61M 2205/3334; A61M 2205/3344
    See application file for complete search history.

(56) References Cited

U.S. PATENT DOCUMENTS

| | | |
|---|---|---|
| 2014/0296740 A1 | 10/2014 | Steinhilper et al. |
| 2015/0320357 A1* | 11/2015 | Kuraguntla ............... A61F 2/07 600/505 |
| 2016/0029956 A1* | 2/2016 | Rowland ................ A61B 5/076 600/302 |

* cited by examiner

METHOD FOR THE MANUFACTURING OF A CARRYING DEVICE, CARRYING DEVICE, SYSTEM FOR DETECTION OF A PHYSICAL PARAMETER AND METHOD FOR DETECTION OF A PHYSICAL PARAMETER

The invention relates to a method for the manufacturing of a carrying device for reception of at least one sensor, a carrying device for reception of at least one sensor, a system for detection and/or measurement of at least one physical parameter and/or chemical composition of a medium and a method for detection and/or measurement of at least one physical parameter and/or chemical composition of a medium.

The implementation of a sensor into a hollow space or the presence of such a device in a hollow space entails an impact on the fluid flowing through the hollow space. The measurement from the outside is often prevented by the nature of the enclosure, e.g. thick, rigid or non-transparent walls. As illustration, the measurement of a fluid's pressure flowing within a pipe or tube typically requires the insertion of a wire-guided sensor or placing the sensor in a space within the sidewall. The drawbacks of these techniques are manifold. Depending on the flow conditions, the added geometrical features may locally alter the measured pressure in such a way that it no longer represents the sought-after quantity. The sensor, typically of electronic nature, may require sophisticated packaging in order to be protected from the fluid. On the other hand, in the case of handling sensitive fluids (e.g. of medical or biological nature such as blood), the inclusion of sharp edges or obstructions in form of a sensor may damage the fluid, rendering a sensible measurement impossible altogether.

It is known that sensors can be directly inserted into fluids contained in hollow spaces. The sensor may be a wireless device, as described in US 20140296740 A1, or tethered via wire, as shown in U.S. Pat. No. 5,902,248 A. Furthermore it is known to locate sensors outside the body that encloses the hollow space with a conventionally machined membrane between sensor and fluid, as shown in U.S. Pat. No. 6,367,333 B1.

Sensor insertion into the fluid may alter the measurement conditions or harm sensitive fluids. Known membranes are limited to thick and/or planar geometries due to the known fabrication methods.

A concrete technical problem is the inclusion of pressure sensors into artificial heart pumps (e.g. left ventricular assist devices), which support or replace the heart function of patients with congestive heart failure. In such a device, the obtained pressure signal could be used to monitor the patient's state and/or to control the left ventricular assist device's pumping speed. Typically, left ventricular assist devices are designed to have as smooth and continuous blood contacting surfaces as possible. Avoiding the formation of small ridges and gaps has proven to be essential in suppressing blood clotting and hemolysis. These features are difficult to avoid for pressure sensors as they require some form of biocompatible, mechanical coupling to the blood. Sensors introduced directly into the fluid are not suitable. Apart from pressure, other fluid properties like temperature or chemical composition (e.g. oxygen saturation of blood) or operation conditions like sedimentation and formation of obstructions are of interest. Aforementioned examples all require some form of physical coupling (e.g. mechanical, thermal or optical) between the inside of the hollow space and the sensor. For a desirable accuracy, sensitivity and robustness of the measurement, the thickness of the coupling is to be minimized, preferably to the micro-range (<10 µm) or smaller, depending on the application.

The problem to be solved by the invention is to provide a method for the manufacturing of a carrying device for a sensor, a carrying device for a sensor, a system and a method which allow the detection of a physical parameter and/or chemical composition without damaging the fluid.

This problem is solved by the subject matter of the method for the manufacturing of a carrying device for reception of at least one sensor as claimed in claim 1, as well as by a carrying device for reception of at least one sensor, a system for detection and/or measurement of at least one physical parameter and/or chemical composition of a medium and a method for detection and/or measurement of at least one physical parameter and/or chemical composition of a medium. Specific embodiments of the invention are claimed by the dependent claims.

According to the first aspect of the invention, a method for the manufacturing of a carrying device for reception of at least one sensor is presented, in which a receiving body with a surface to be coated is provided. In the receiving body, a space is provided which is open on the side of this surface. A second body with a sealing surface is provided. The second body may particularly be a solid body or a gas-filled or gas-fillable device that provides a sealing surface. The term "sealing" designates impermeability to liquids and paste-like materials in the context of the sealing surface of the second body. This sealing surface is positioned in such a manner that the surface to be coated of the receiving body is sealed by the second body at least in the circumference of the space in the receiving body. Thereby, the shape of the sealing surface of the second body adapts complementary to the surface to be coated of the receiving body. A formable or moldable filling material is provided in the space in such a manner that the filling material forms a surface shaped complementary to the sealing surface of the second body, closing the space. At least the volume of the filling material contacting the sealing surface of the second body is solidified. Depending on the filling material used, the step of solidifying may be implicit in the step of providing a filling material. That is, if the filling material is e.g. a formable material, such as a wax, it may provide a solid surface on the sealing surface of the second body after filling it into the space without an additional solidifying step. The sealing surface of the second body is removed from the surface to be coated as well as from the surface provided by the filling material. The surface to be coated is coated such that a membrane is provided, sealing the space. After the described steps, the membrane is suspended over the space, which can be a sensor recess. The coating may particularly be applied through chemical vapor deposition (CVD), atomic layer deposition (ALD), dip-coating or another suitable process.

In one embodiment of the invention, the filling material is at least partially removed after the coating process. Particularly, it may be completely removed. However, as the sensor may be embedded in the filling material, it may be sufficient to remove only parts of the filling material. Alternatively, the filling material may entirely remain in the space in the receiving body. Particularly, the filling material is removed through dissolving and/or melting, e.g. by immersion in a deionized water bath at elevated temperature or dissolving by acid or alkaline solutions.

In one embodiment of the invention, the receiving body encloses a hollow space, in particular a hollow cylinder, of which the interior surface is to be coated.

The space in the receiving body may be realized by a continuous opening. It may be manufactured through drilling, broaching, electrochemical machining (ECM), and/or other techniques.

In another embodiment of the invention, the sealing surface of the second body is positioned by pressing it against the surface to be coated due to a change of the temperature of at least one of the receiving body and the second body and a corresponding expansion or contraction process of the respective body, and/or due to inflating the second body or parts thereof. In the case of a receiving body that encloses a hollow space, the second body may be a core element of which the cross section is essentially of the same shape and size as the cross section of the hollow space of the receiving body. Different thermal expansion or contraction processes may be used in order to position and interlock the core element inside the hollow space defined by the receiving body, sealing it with the sealing surface of the second body. The outer surface of the core element forms a tight seal with the inner surface of the receiving body, at least in the circumference of the space in the receiving body.

In one embodiment, the material of the second body has a higher coefficient of thermal expansion (CTE) than the material of the receiving body. The core element is inserted into the hollow space. At least the inserted core is heated to an elevated temperature, which is referred to as interlocking temperature, such that—due to thermal expansion—the core element is interlocked in the hollow space.

In another embodiment, the core element and the receiving body are heated to achieve interlocking, wherein due to different coefficients of thermal expansion the core element is interlocked in the hollow space.

Alternatively, the core element or the receiving body including the core element is cooled prior to insertion of the core element into the hollow space. Interlocking then occurs during reheating of the respective body, e.g. to room temperature. An advantage of this embodiment is that the differing thermal expansion coefficients can further be exploited and the requirements for machining tolerances can be lowered. Besides, the interlocking can be realized without heating above room temperature.

In another embodiment, the coefficient of thermal expansion of the material of the core element is lower than the coefficient of thermal expansion of the receiving body. In this case, the receiving body with or without the core element is cooled to achieve interlocking.

Alternatively, the receiving body or both, receiving body and core element, is/are heated prior to insertion of the core element into the hollow space. In this case, interlocking occurs during cooling of the respective body/bodies.

In another embodiment, the receiving body is heated prior to insertion of the second body. In this case, interlocking occurs through thermal contraction of the receiving body when cooled down.

In still another embodiment, the second body may be a hollow, elastic, balloon-like inflatable device that is inflated by exerting a pressure onto the interior of this device and/or by introducing a fluid into the interior of this device in order to seal the surface to be coated. Prior to inflation, the dimensions of said balloon-like device may be significantly smaller than the hollow space, which enables to reach hollow spaces that are difficult to access due to their geometry. Furthermore, the interlocking becomes temperature independent and thus a greater choice of materials for the filling material is possible.

However, the present invention is not restricted to only one of the mentioned embodiments, but a shrinking process of the receiving body may be combined with inflation of the inflatable device in order to press the sealing surface of the second body against the surface to be coated.

In a simple embodiment, the sealing surface of the second body may be pressed against the surface to be coated such that a sealing effect is achieved between the receiving body and the second body.

Prior to positioning the second body, additional coatings or agents could be realized or applied onto the receiving body and/or the second body to facilitate the positioning of the sealing surface on the surface to be coated, in case of a hollow cylinder to facilitate the insertion and removal of the core element.

Besides, adhesion promoting coatings could be applied onto the receiving body prior to coating for better adhesion of the membrane. Furthermore, coatings and/or depositions onto the membrane are possible that enhance or enable additional sensing functionality or improve the structural robustness.

Particularly, the filling material is inserted into the space in the receiving body in a liquid or paste-like state and is at least partially solidified, namely at the side of the surface to be coated, by cooling or heating and/or curing. That is, the filling material may be a liquid, paste-like or powdery medium which is at least partially solidified by cooling down, heating or curing. Particularly, the filling material is a thermoplastic or thermosetting organic substance or a thermoplastic or thermosetting mixture of organic substances, e.g. a wax that is cooled below its melting point. Said wax is given into the space in the receiving body and hardened while the receiving body and the core element are still interlocked, forming a wax surface in the surface to be coated that is flush with the surface to be coated of the receiving body.

In another embodiment, the filling material may be a thermosetting material, e.g. a synthetic resin, which is cured. Curing may be initiated, accelerated and/or enhanced through heating, irradiation or addition of chemicals and/or humidity.

In another embodiment, the sealing surface of the second body is removed from the surface to be coated as well as from the surface provided by the filling material by contraction of the second body due to reduction of temperature of the second body and/or pressure reduction in the second body. That is, the volume or cross section of the second body is reduced by thermal contraction and/or by reduction of pressure or volume of a fluid contained in an inflatable device providing the second body.

A second aspect of the invention describes a carrying device for reception of at least one sensor, comprising a receiving body with a space provided in the receiving body, wherein said space is suitable to receive at least one sensor. Said space is open on a surface of the receiving body. The carrying device further comprises a membrane that seals said surface of the receiving body at least partially and closes the opening of the space in the surface. Particularly, the carrying device is manufactured with a method according to the first aspect of the invention and/or at least one of the embodiments described.

One advantage is the seamless integration of the arbitrary shaped membrane suspended over the space according to the invention. The carrying device which may be an enclosure forming a hollow space, e.g. a pipe, tube, etc., may be fabricated in any applicable manner and from any material.

In one embodiment, the membrane is positioned in such a manner that it is flush with the surface to be coated of the receiving body. Particularly, the membrane thickness is less than 10 μm. The membrane can be made of any material which does not interfere with the measurement principle of the sensor and can be coated as a conformal film onto the surface to be coated. For example, if the analyte's pressure is to be measured, the material's Young's Modulus needs to be low enough to allow enough deflection of the diaphragm, such that the pressure may be transmitted to the sensor.

In a further embodiment, the membrane essentially covers the whole surface providing the opening of the space of the receiving body. That is, the membrane may totally cover the whole surface providing the opening of the space of the receiving body.

Particularly, the membrane material is poly(p-xylylene) (Parylene). Parylene is biocompatible such that the medium could be of biological nature (e.g. blood).

A third aspect of the invention describes a system for detection and/or measurement of at least one physical parameter and/or chemical composition of a medium, in particular of a fluid, comprising the carrying device for reception of at least one sensor according to the second aspect of the invention or at least one of the described embodiments and at least one sensor positioned in the space of the receiving body of the carrying device. Particularly, the sensor is fixed in the opening.

Particularly, when the receiving body of the carrying device of the system for detection and/or measurement provides a hollow space, a medium in form of a liquid or a gas may be conducted through the hollow space and at least one physical parameter and/or chemical composition of the medium such as velocity or pressure may be measured.

Detection and/or measurement of a chemical composition may comprise qualitative and/or quantitative methods for the detection or measurement of chemical elements and/or compounds. That is, for example, the presence of a substance may be detected using a qualitative method, or the blood oxygen concentration may be measured using a quantitative method.

In one embodiment, the system for detection and/or measurement may be applied onto a body to be able to measure a parameter such as frequency, e.g. a heart rate.

The sensor may be embedded in filling material contained in the space in the receiving body.

In another embodiment, sensor and membrane are positioned in a distance to each other. The distance between the sensor and the membrane may at least partially be filled with a coupling medium, which is able to transmit physical parameters such as pressure, oscillations, etc. The membrane is thin and soft, such that its restoration force does not significantly impede the accuracy of or sensitivity of the sensor. Particularly, silicone oil may be used.

Alternatively, the sensor directly contacts the membrane.

The claimed system may exemplarily be used for pressure measurements. In this case, the sensor may e.g. be realized as a piezo-resistive microelectromechanical system pressure sensor which is positioned into the space in the carrying device.

A fourth aspect of the invention describes a method for detection and/or measurement of at least one physical parameter and/or chemical composition of a medium, in particular of a fluid, wherein a system for detection and/or measurement according to the invention is provided. Additionally, the medium, of which at least one physical parameter and/or chemical composition is to be detected and/or measured, is provided. The medium is positioned with respect to the system for detection and/or measurement in such a manner that at least one physical parameter and/or chemical composition of the medium can be detected and/or measured by means of the sensor. Subsequently, at least one physical parameter and/or chemical composition of the medium is detected and/or measured.

Also in this aspect, when the receiving body of the carrying device of the system for detection and/or measurement provides a hollow space, a medium in form of a liquid or a gas may be conducted through the hollow space and at least one physical parameter and/or chemical composition of the medium such as velocity or pressure may be measured.

In another embodiment of this aspect, the system for detection and/or measurement may be applied onto a body to measure a parameter such as oscillation frequency, e.g. a heart rate.

The main advantage of the invention is the manufacturing of a system that allows for the perturbation-free measurement of fluid properties and operating conditions. The possible membrane geometries and properties do not limit its use to a single type of measurement (e.g. pressure). The membrane material and fabrication process may be chosen in such way that biocompatibility is achievable.

With respect to the example of measurement in left ventricular assist devices or blood contacting medical devices in general, the invention avoids physiological side effects, like blood clotting and hemolysis; it avoids drift of functional properties of the sensors.

The invention is not limited to the alternatives described herein. Furthermore, all described embodiments and alternatives of the invention may be combined.

The invention is further illustrated and characterized by the following figures that show a certain example from which further embodiments and advantages can be drawn. These figures are meant to illustrate the invention but not to limit its scope.

FIGS. 1a)-d) show procedural steps of a method according to the invention.

Figure 2:
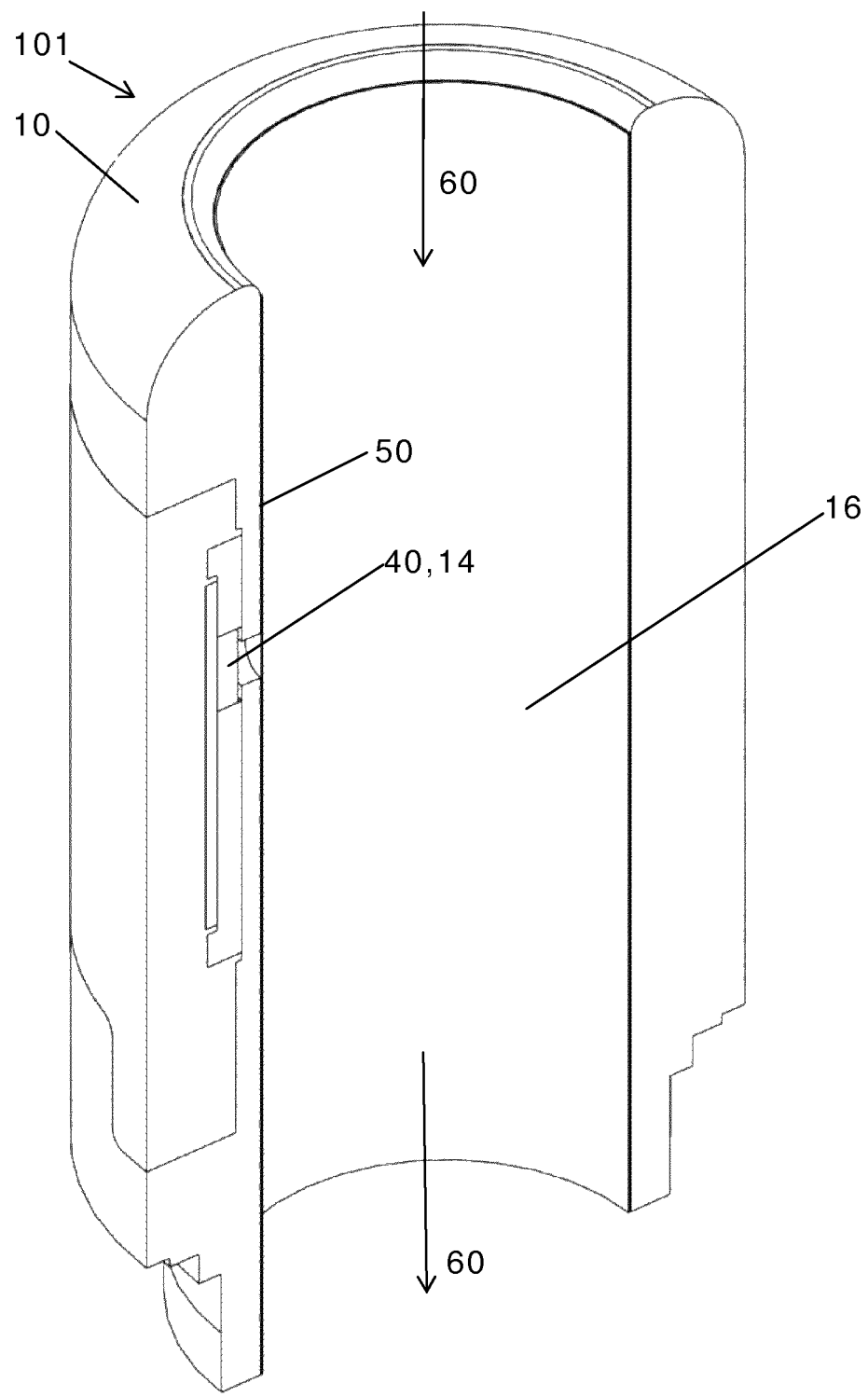

FIG. 2 shows a perspective view of an inflow cannula of a left ventricular assist device.

FIG. 1a) shows the cross-section of a carrying device 1. The receiving body 10 is realized as a hollow cylinder 16, so the carrying device 1 has a tubular cross-section, at least in the area presented. In this example, the receiving body 10 may be of steel or titanium. The space 14 is realized as continuous opening 141 in the form of a drill hole, of which the outer part has a bigger diameter than the inner part. The size of the space 14 is predetermined by the size of the sensor 40 that is to be inserted into the continuous opening 141.

The surface to be coated 12 is located on the inside of the hollow cylinder 16. That is, in this example, the entire inner surface of the hollow cylinder 16 is to be coated. A second body 20 is positioned inside the hollow cylinder 16. It comprises a sealing surface 22 on the outside, which is in sealing contact with the surface to be coated 12 of the receiving body 10.

In this example, the second body is of a material with a higher coefficient of thermal expansion than the material of the first body. The insertion of the second body 20 was carried out at room temperature. Both bodies are manufactured to such tolerances that insertion is feasible at room temperature. Subsequently, the entire assembly, comprising both the receiving body 10 and the second body 20, was heated to a higher temperature, referred to as interlocking temperature, to achieve interlocking of the second body 20 and the receiving body 10. Interlocking is to be achieved in such a way that the surface to be coated 12 is sealed.

FIG. 1b) shows the same cross-section with a filling material 30 positioned in the space 14 of the receiving body 10. The second body 20 is still interlocked with the receiving body 10, as the temperature is still equal or above the interlocking temperature.

The filling material 30 in this example is a wax with a higher melting point than the interlocking temperature. It was filled inside the space 14 and solidified by letting cool to a temperature below its melting point, but above the interlocking temperature. The solidified filling material 30 forms a surface shaped complementary to the sealing surface 22 of the second body 20.

FIG. 1c) shows the same cross-section, where the second body 20 is removed and the surface to be coated 12 is covered with a membrane 50.

The whole assembly comprising the receiving body 10, the second body 20 and the solidified filling material 30 was cooled to a temperature below the interlocking temperature. Subsequently, the second body 20 was removed. A membrane 50 consisting of Parylene was deposited onto the surface to be coated 12 of the receiving body 10 in a room-temperature coating process. That is, in this example, the entire inner surface of the hollow cylinder 16 is coated with a Parylene membrane 50 of which the thickness is less than 10 µm.

FIG. 1d) shows the same cross-section, where the filling material 30 is removed. The membrane 50 separates the space 14, i.e. the continuous opening 141, of the receiving body 10 from the hollow cylinder 16. The receiving body 10 is now ready to receive a sensor 40 which is to be inserted into the continuous opening 141. The surface of the membrane 50 is smooth, as it covers the entire inner surface of the receiving body 10. There are no obstructions in the hollow cylinder 16 which could damage or disturb a medium 60 flowing through said hollow cylinder 16. Besides, the sensor 40 is enabled to perform accurate and robust measurements through the thin and transparent Parylene membrane 50.

FIG. 2 shows an inflow cannula 101 of a left ventricular assist device as a receiving body. The membrane 50 is located on the inner surface of the receiving body 10 that forms a hollow cylinder 16. A sensor 40 is positioned in the space 14. The membrane 50 covers the hollow cylinder 16 which is provided by the inflow cannula 101 of the left ventricular assist device and separates the space 14, containing the sensor 40, from the medium 60 that flows through said inflow cannula 101. This example shows the inserted sensor 40 that is enabled to perform accurate and robust measurements through the thin and transparent Parylene membrane 50. Furthermore, as also in this example the membrane 50 covers the entire inner surface of the receiving body 10, no obstructions are present in the hollow cylinder 16 which could damage or disturb the medium 60 that flows through the inflow cannula 101 of the left ventricular assist device. This example enables the measurement of blood pressure and, thus, allows for monitoring the patient's state and for controlling the left ventricular assist device's pumping speed.

LIST OF REFERENCE SIGNS 1 carrying device
10 receiving body
12 surface to be coated
14 space
16 hollow cylinder
20 second body
22 sealing surface
30 filling material
40 sensor
50 membrane
60 medium
101 left ventricular assist device inflow cannula
141 continuous opening

The invention claimed is:

1. A method for the manufacturing of a carrying device (1) for reception of at least one sensor (40), comprising the steps of:
providing a receiving body (10) having a surface to be coated (12) and a space (14) which is open on the side of this surface,
providing a second body (20) having a sealing surface (22) and positioning the sealing surface (22) of the second body (20) in such a manner that the surface to be coated (12) of the receiving body (10) is sealed by the second body (20) at least in a circumference of the space (14) in the receiving body,
providing a formable or moldable filling material (30) in the space (14) in such a manner that the filling material (30) forms a surface shaped complementary to the sealing surface (22) of the second body (20) closing the space (14),
solidifying at least the volume of the filling material (30) contacting the sealing surface (22) of the second body (20),
removing the sealing surface (22) of the second body (20) from the surface to be coated (12) as well as from the surface provided by the filling material (30),
coating the surface to be coated (12) such that a membrane (50) is provided sealing the space (14).

2. Method for the manufacturing of a carrying device (1) according to claim 1, wherein the filling material (30) is at least partially removed after the coating process.

3. Method for the manufacturing of a carrying device (1) according to claim 1, wherein the receiving body (10) encloses a hollow space.

4. Method for the manufacturing of a carrying device (1) according to claim 1, wherein the space (14) in the receiving body is realized by a continuous opening (141).

5. Method for the manufacturing of a carrying device (1) according to claim 1, wherein the sealing surface (22) of the second body (20) is positioned by pressing it against the surface to be coated (12) due to a change of the temperature of at least one of the receiving (10) and second body (20) and a corresponding expansion or contraction process of the respective body, and/or due to inflating the second body (20) or parts thereof.

6. Method for the manufacturing of a carrying device (1) according to claim 1, wherein the filling material (30) is inserted into the space (14) in the receiving body (10) in a liquid or paste-like state and is at least partially solidified by cooling or heating and/or curing.

7. Method for the manufacturing of a carrying device (1) according to claim 1, wherein the sealing surface (22) of the second body (20) is removed from the surface to be coated (12) as well as from the surface provided by the filling material (30) by contraction of the second body (20) due to reduction of temperature of the second body (20) and/or pressure reduction in the second body (20).

* * * * *